(12) United States Patent
Polonsky et al.

(10) Patent No.: US 8,557,529 B2
(45) Date of Patent: Oct. 15, 2013

(54) NANOPORE CAPTURE SYSTEM

(75) Inventors: Stanislav Polonsky, Putnam Valley, NY (US); Ali Afzali-Ardakani, Ossining, NY (US); Hongbo Peng, Tianmen (CN); Gustavo A. Stolovitzky, Riverdale, NY (US); Ajay A. Royyuru, Congers, NY (US); Mark N. Wegman, Westchester, NY (US)

(73) Assignee: International Business Machines Corporation, Armonk, NY (US)

( * ) Notice: Subject to any disclaimer, the term of this patent is extended or adjusted under 35 U.S.C. 154(b) by 142 days.

(21) Appl. No.: 12/757,433

(22) Filed: Apr. 9, 2010

(65) Prior Publication Data

US 2011/0250705 A1 Oct. 13, 2011

(51) Int. Cl.
*C12Q 1/68* (2006.01)

(52) U.S. Cl.
USPC .......................................................... 435/7.1

(58) Field of Classification Search
None
See application file for complete search history.

(56) References Cited

U.S. PATENT DOCUMENTS

| | | | |
|---|---|---|---|
| 6,133,046 A | 10/2000 | Clerc | |
| 6,548,311 B1 | 4/2003 | Knoll | |
| 6,835,552 B2 | 12/2004 | Miles et al. | |
| 7,132,275 B2 | 11/2006 | Reich et al. | |
| 7,195,780 B2 | 3/2007 | Dennis et al. | |
| 7,439,055 B1 | 10/2008 | Huo et al. | |
| 2004/0106121 A1 | 6/2004 | Ugolin et al. | |
| 2004/0197793 A1* | 10/2004 | Hassibi et al. | 435/6 |
| 2007/0190656 A1 | 8/2007 | Crain et al. | |
| 2008/0171316 A1 | 7/2008 | Golovchenko et al. | |
| 2008/0187915 A1* | 8/2008 | Polonsky et al. | 435/6 |
| 2009/0023146 A1 | 1/2009 | Harnack et al. | |
| 2009/0036315 A1 | 2/2009 | Labgold et al. | |
| 2011/0226622 A1* | 9/2011 | Hino et al. | 204/469 |

OTHER PUBLICATIONS

Fixe et al Nanotechnoloy (2005) 16: 2061-2071.*
Polonsky et al, IBM Research Report "DNA Transistor," Apr. 18, 2007.

* cited by examiner

*Primary Examiner* — Mark Shibuya
*Assistant Examiner* — Richard Moerschell
(74) *Attorney, Agent, or Firm* — Ido Tuchman; William J. Stock

(57) ABSTRACT

A nanopore capture system may include a material configured to pass through a nanopore device in a controlled manner based upon its interaction with the nanopore device. The system may also include a capture mechanism connected to one end of the material. The capture mechanism may be configured to catch a particular type of molecule while ignoring other types of molecules. The system may also include a controller to manipulate and/or detect the particular type of molecule.

10 Claims, 14 Drawing Sheets

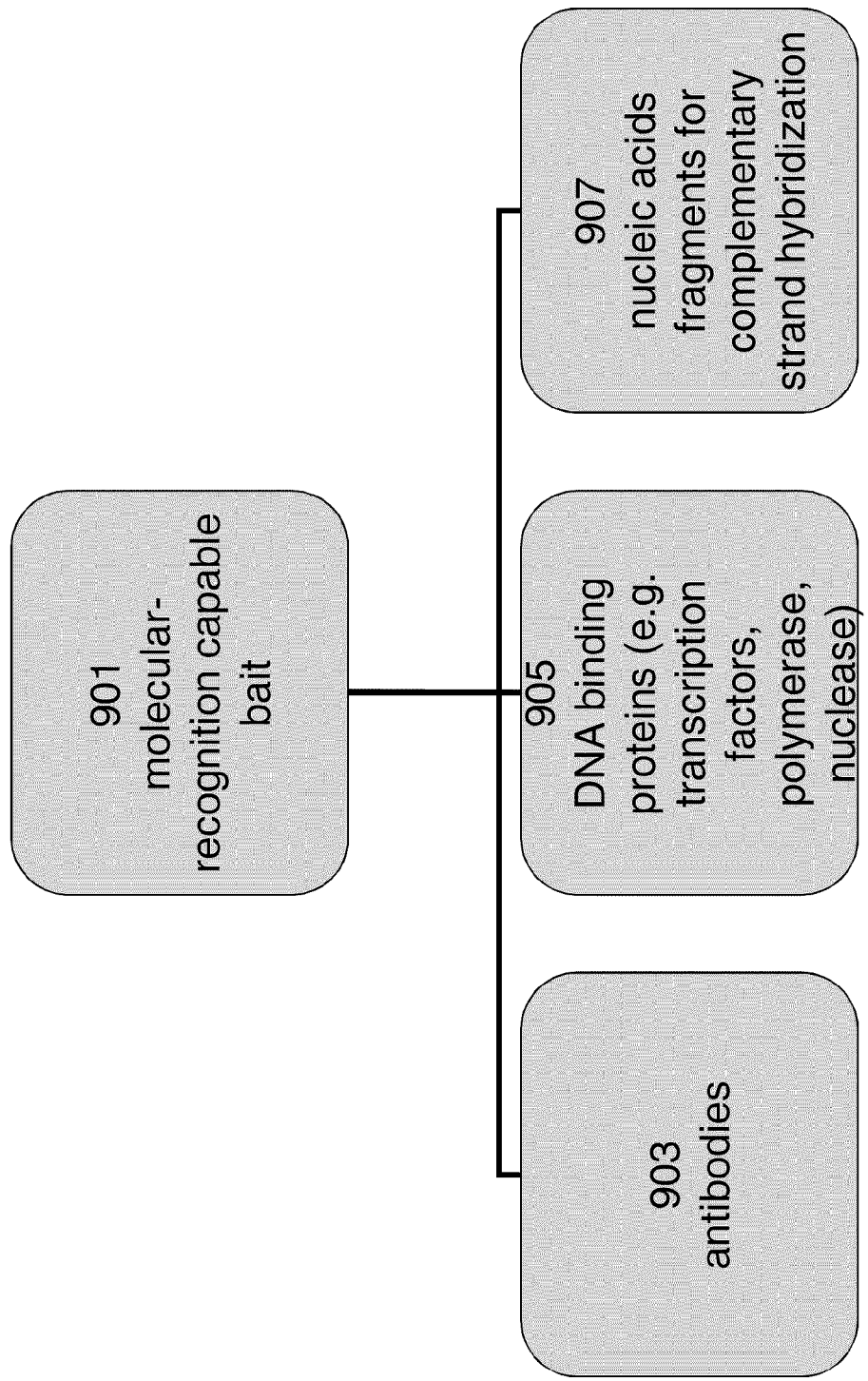

NANOPORE CAPTURE SYSTEM

RELATED APPLICATIONS

This application contains subject matter related to the subject matter of a co-pending application entitled "Systems and Methods for Controlling the Position of a Charged Polymer Inside a Nanopore" and having U.S. Publication No. 2008/0187915, the entire subject matter of which is incorporated herein by reference in its entirety. The aforementioned application is assigned to the same assignee as this application, International Business Machines Corporation of Armonk, N.Y.

BACKGROUND

1. Field of the Invention

The invention relates to the field of nanopores, and, more particularly, to nanopore systems.

2. Description of Background

Generally, a nanopore is a hole of a predetermined size in a solid material or a protein pore in a biological membrane. The nanopore is formed or fabricated in a solid material may be sized according to its intended use. The nanopore may be, for example, drilled or etched into the solid material.

Nanopore systems are being developed for use in sensing and controlling molecules and/or bio-molecules. In such systems, the nanopore is usually sized to have an inner diameter slightly larger than the outer diameter of the molecule being studied.

SUMMARY

An example embodiment of the present invention is a nanopore regulation system. The system may include a material configured to traverse a nanopore opening in a solid state membrane device in a controlled manner based upon its interaction with the solid state membrane device. The nanopore opening may be sized to limit the passage of a particular molecule through it. The system further includes a capture mechanism connected to one end of the material. The capture mechanism is configured to bond to a particular type of molecule while not bonding to other types of molecules.

The system may also include a first electrode adjacent one side of the nanopore opening, and a second electrode adjacent the other side of the nanopore opening. The first electrode and the second electrode may be configured to regulate the material's position with respect to the nanopore device. Moreover, the second electrode may interact with the first electrode to produce an electric field that regulates and monitors the passage of the particular molecule through the nanopore opening.

The material may include a polymer and/or a non-biological molecule. The polymer may comprise a polypeptide. The system may also include a controller to detect the particular molecule and/or manipulate the particular molecule's location. The controller may detect the particular molecule based upon voltage changes in control electrodes and/or ionic current changes.

The capture mechanism may include an antibody, a deoxyribonucleic acid binding protein, a nucleic acid or peptide aptamer, an oligonucleotide, and/or nucleic acid fragments for complementary strand hybridization. The controller may process the particular molecule.

The controller may destroy the particular molecule. The system may include a reservoir adjacent at least one side of the nanopore device that is flushed after the particular molecule is destroyed.

The system may include a first electrode adjacent one side of the nanopore device, and a second electrode adjacent the other side of the nanopore device.

Another example embodiment of the present invention is a nanopore capture system method. The method may include connecting a capture mechanism to one end of a material, with the capture mechanism configured to catch a particular type of molecule while ignoring other types of molecules. The method may also include controlling the passage of the material through a nanopore device based upon the material's interaction with the nanopore device.

The method may further include detecting the particular molecule, manipulating the particular molecule's location, and/or processing the particular molecule with a controller. The method may additionally include regulating the material's position with respect to the nanopore device with a first electrode and a second electrode.

The method may further include destroying the particular molecule. The method may additionally include using at least one of voltage changes in control electrodes and ionic current changes to detect the particular molecule.

Another example aspect of the invention is an embodiment in which a polymer material may be configured to pass through a nanopore device in a controlled manner based upon its interaction with the nanopore device. The embodiment may include a capture mechanism connected to one end of the polymer material, with the capture mechanism configured to catch a particular type of molecule while ignoring other types of molecules. The embodiment may also include a controller to detect the particular molecule and/or manipulate the particular molecule's location.

Another aspect of the invention is an embodiment in which a material may be configured to pass through a nanopore device in a controlled manner based upon its interaction with the nanopore device. The embodiment may include a capture mechanism connected to one end of the material, with the capture mechanism configured to catch a particular type of molecule while ignoring other types of molecules. The embodiment may also include a controller to detect the particular molecule and/or manipulate the particular molecule's location based upon voltage changes in control electrodes and/or ionic current changes.

BRIEF DESCRIPTION OF THE DRAWINGS

FIG. 7 is exemplary embodiments of some bait species capable of molecular recognition for the nanopore capture system of FIG. 1.

DETAILED DESCRIPTION

Example embodiments of the invention will now be described more fully hereinafter with reference to the accompanying drawings, in which preferred embodiments of the invention are shown. Like numbers refer to like elements throughout, like numbers with letter suffixes are used to identify similar parts in a single embodiment, and letter suffix lower case n is a variable that indicates an unlimited number of similar elements.

Figure 1:
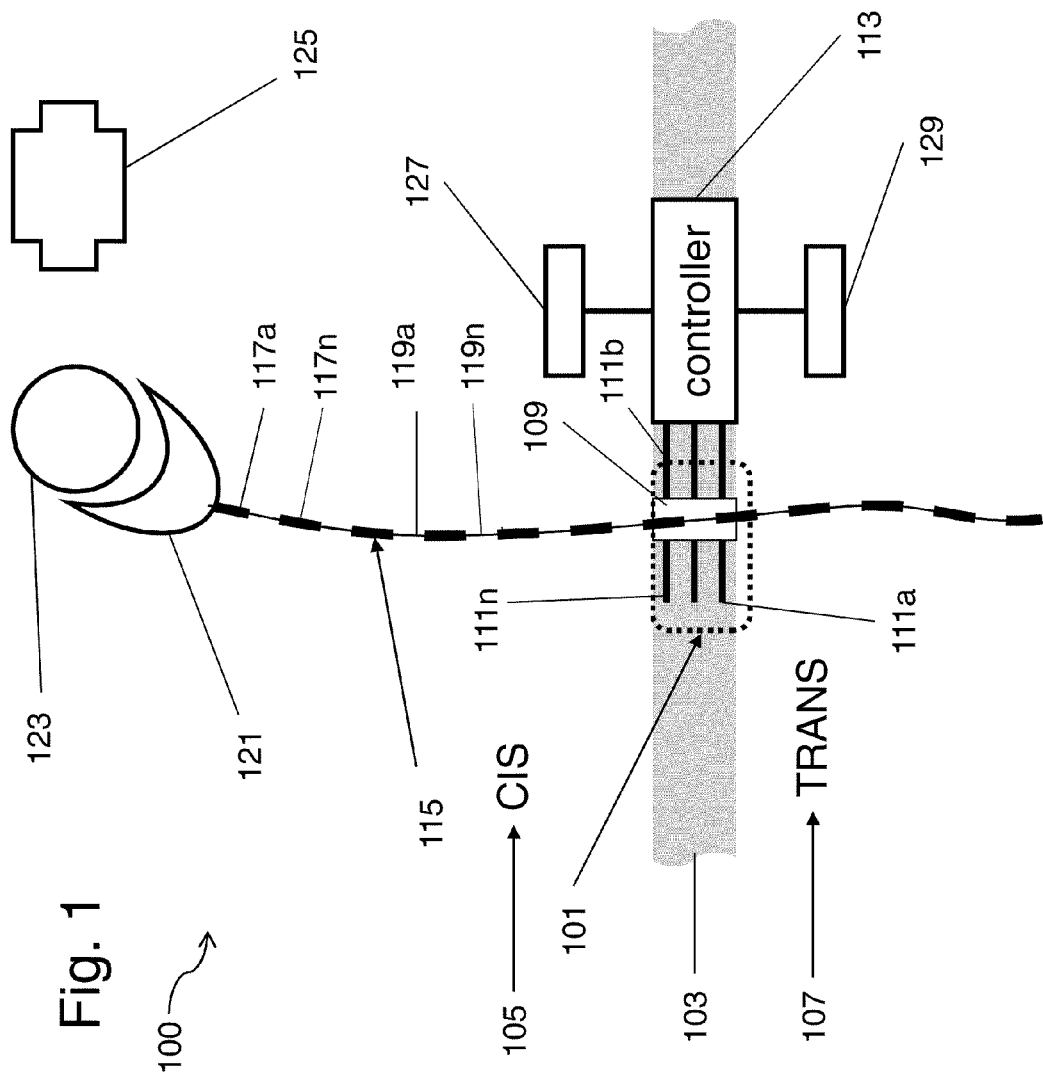
FIG. 1 is a schematic block diagram of a nanopore capture system in accordance with the invention.

With reference now to FIG. 1, a nanopore capture system 100 is initially described. According to one embodiment of the invention, the system 100 includes a material 115 configured to pass through a nanopore device 101 in a controlled manner based upon its interaction with the nanopore device. The system 100 also includes a capture mechanism 121 connected to one end of the material 115. In one embodiment, the capture mechanism 121 is configured to catch a particular type of molecule 123 while ignoring other types of molecules 125.

In one embodiment, the material 115 includes a polymer and/or a non-biological molecule. In another embodiment, the polymer comprises a polypeptide.

In one embodiment, the system 100 includes a controller 113 to detect the particular molecule 123 and/or manipulate the particular molecule's location. In another embodiment, the controller 113 detects the particular molecule 123 based upon voltage changes in control electrodes 111a-111n and/or ionic current changes.

In one embodiment, the capture mechanism 121 includes an antibody, a deoxyribonucleic acid binding protein, an oligonucleotide, an aptamer and/or nucleic acid fragments for complementary strand hybridization. In another embodiment, the controller 113 processes the particular molecule 123. The detail description begins with introducing all the elements in relation to the drawings. Then the detail description discloses the nuts and bolts of the functionality of the invention.

For example, the controller 113 processes the particular molecule 123 by destroying the particular molecule. In one embodiment, the system 100 includes a CIS reservoir 105 adjacent one side of the nanopore device 101 that is flushed after the particular molecule 123 is destroyed.

In one embodiment, the system 100 includes a first electrode 127 adjacent one side of the nanopore device 101, and a second electrode 129 adjacent the other side of the nanopore device. In another embodiment, the first electrode 127 and the second electrode 129 are configured to regulate the material's 115 position with respect to the nanopore device 101.

In one embodiment, FIG. 1 illustrates the nanopore device 101 or stator (stationary part) of a single-molecule linear motor situated inside a solid state membrane 103 separating a CIS reservoir 105 and a TRANS reservoir 107. The nanopore device 101 consists of a nanopore 109 and several control electrodes 111a-111n.

In one embodiment, the controller 113 is capable of applying voltages to control electrodes 111a-111n as well as measuring voltages induced in these electrodes. The controller 113 can be integrated in or near the membrane 103 or can stand alone.

In one embodiment, the material 115 or armature (moving part) of the linear motor is a single molecule of charged linear polymer. In another embodiment, the thick segments 117a-117n represent charges on the polymer chain and thin segments 119a-119n represent neutral parts of the chain. In addition, as described in U.S. Patent Publication No. 2008/0187915, the nanopore device 101 can control the position of the material 115 along the longitude axis of nanopore 109 with resolution better than the distance between charges in the polymer chain. Additionally, the nanopore device can position the material 115 by stopping its passage through the nanopore 109, locking this stopped position for a period of time, and then start the material 115 moving again through the nanopore 109.

In one embodiment, one end of material 115 is functionalized with a catching mechanism 121, e.g. a molecule, which is capable of molecular recognition of other molecular species such as particular molecule 123. In another embodiment, molecular recognition refers to specific interaction between these two molecules through non-covalent bonding. In another embodiment, all other molecular species, such as molecule 125, different from particular molecule 123, do not bind to catching mechanism 121.

In one embodiment, when particular molecule 123 binds to catching mechanism 121, the nanopore device 101, e.g. stator, controlled by controller 113, is capable of moving particular molecule 123 and anything else that can, in turn, be attached to it. For example, this can be a virus, a cell, fragment of a cell, and/or the like. Using a fishing analogy, the material 115 can be thought of as "fishing string", the catching mechanism 121 as "bait", and the particular molecule 123 as a "catch" or "prey."

In one embodiment, the system 100 can have multiple nanopores 109 that can share a single controller 113. In another embodiment, multiple controllers 113 can connect to multiple nanopores 109.

In one embodiment, a drag electrode 127 located in CIS reservoir 127 and a drag electrode 129 located in TRANS reservoir 107, and not inside the nanopore 109, apply a voltage difference between the CIS reservoir and the TRANS reservoir to attract fishing strings, e.g. material 115, inside the nanopore 109. In another embodiment, the voltage at the drag electrodes 127 and 129 is set by controller 113.

Figure 2:
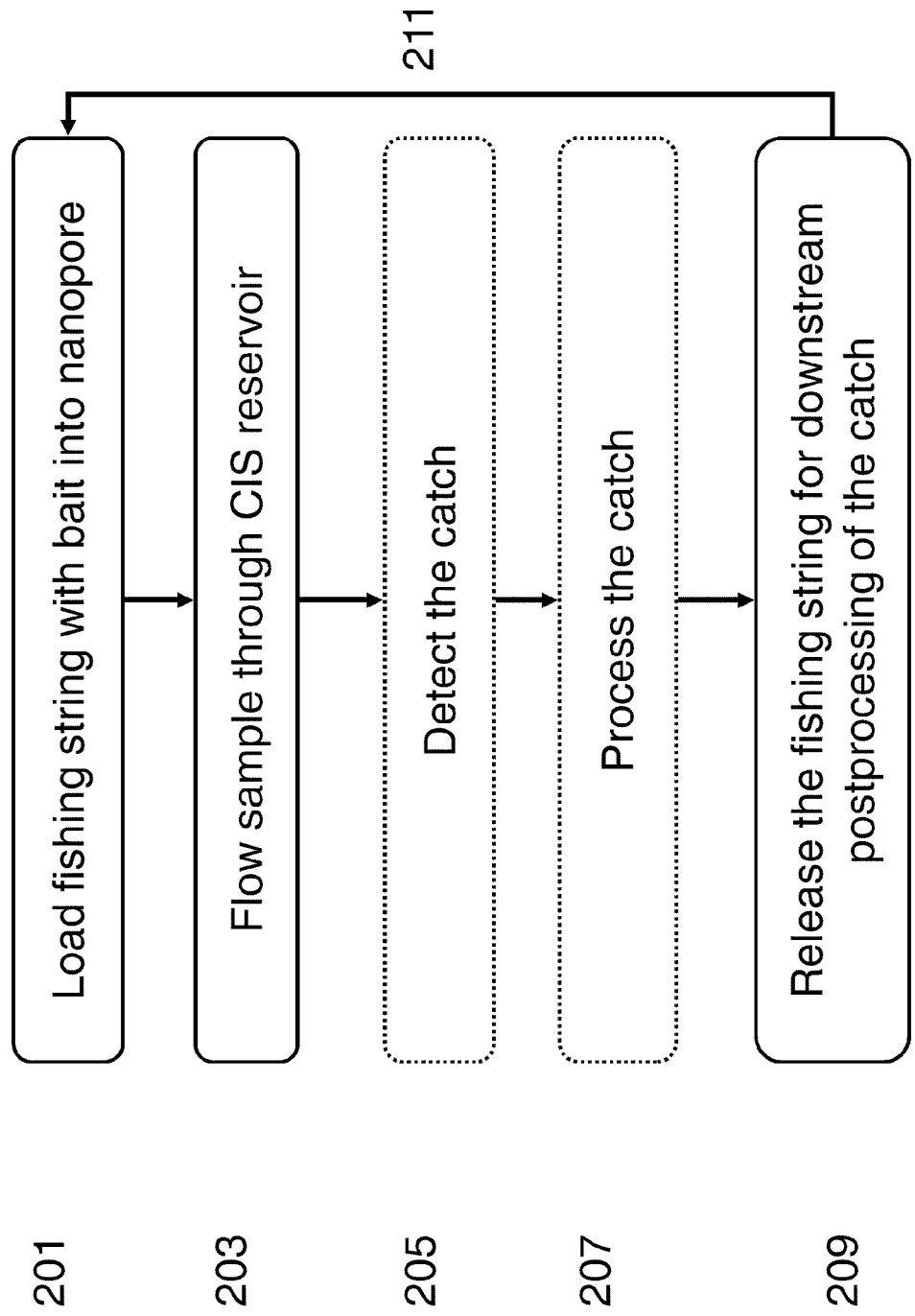
FIG. 2 is a flowchart illustrating method aspects according to the invention.

With additional reference to the block diagram of FIG. 2, the operation of one embodiment of system 100 is outlined. The fishing strings 115 with bait 121 are flown in (loaded into) CIS reservoir 105 and loaded (pulled into) in nanopores 109 by a voltage difference between drag electrodes 127 and 129 at Block 201. Once the fishing strings 115 reside in the nanopores 109, the catch 123 and, possibly, other molecular species are flown through the CIS reservoir 105 at Block 203.

It is noted that steps 201 and 203 should not necessary be sequential. In fact, the steps 201 and 203 can overlap or even occur simultaneously.

Figure 3:
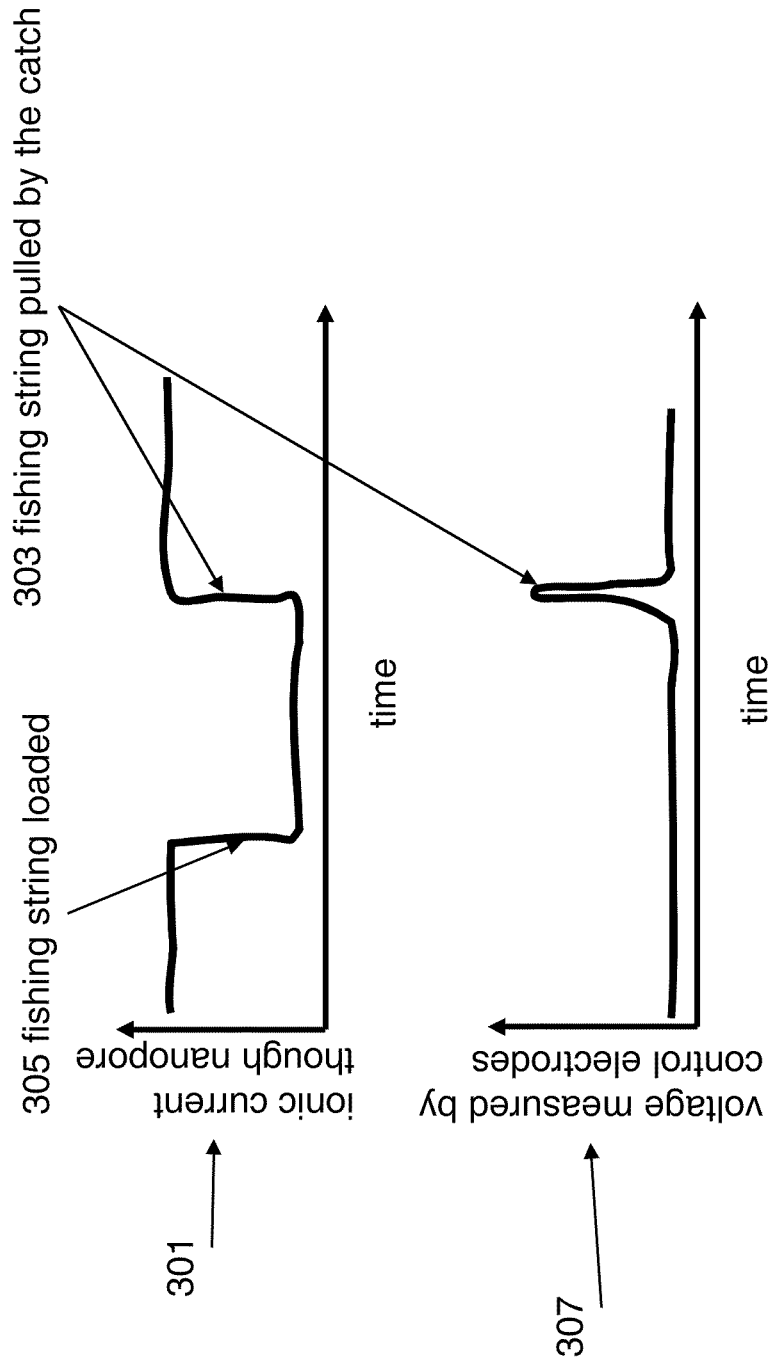
FIG. 3 is a graphical representation of electronically detecting the catch with the nanopore capture system of FIG. 1.

In one embodiment, the binding of a catch 123 is detected electronically at Block 205. For example, if the catch 123 is large enough, the viscous drag applied by the liquid flow on the catch can overcome the electric force that keeps the fishing string 115 inside the nanopore 109 as illustrated in FIG. 3.

In one embodiment, such an event can be detected when the ionic current 301 between the drag electrodes 127 and 129, and/or control electrodes 111a-111n changes at step 303, returning to the level before the fishing string 115 was loaded at step 305.

In another embodiment, when the catch 123 starts to pull the fishing string 115 out of the nanopore 109, its charges pass by control electrodes 111a-111n and induce transient voltage pulses 307. The controller 113 detects such a pulse and, optionally, adjusts the voltages applied to the linear motor to keep the fishing string 115 inside the nanopore 109.

It is noted that not each catch 123 species can be detected electronically. In other cases, the detection of catch 123 is not needed. The optional character of this step is indicated by the dashed line of Block 205.

Figure 4:
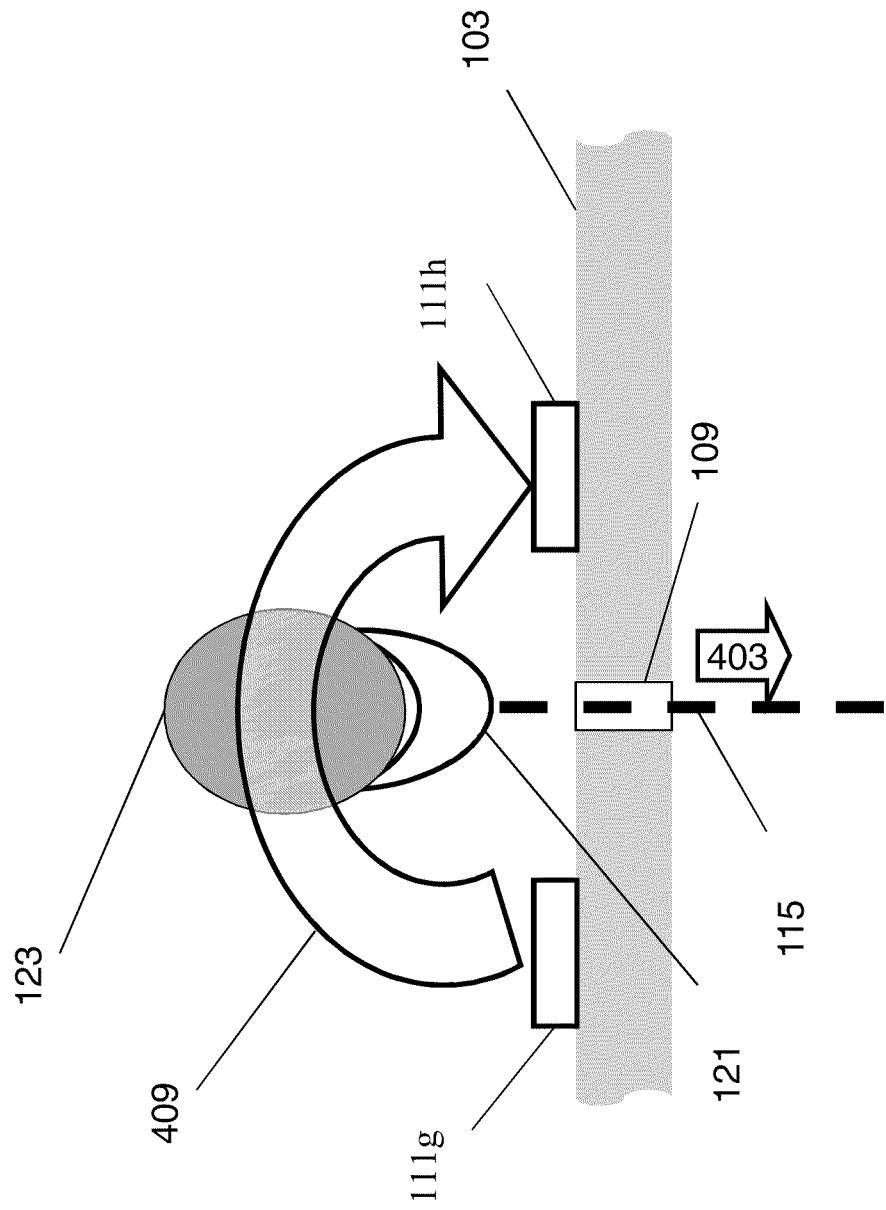
FIG. 4 is a graphical representation of processing the catch with the nanopore capture system of FIG. 1.

Also optional is the next step—processing of the catch 123 at Block 207. In one embodiment, illustrated in FIG. 4, the catch is a pathogen, e.g. particular molecule 123, slated for destruction. Once the catch 123 binding is detected, the stator 101 pulls the fishing string 115 inside the nanopore 109, as indicated by arrow 403, and brings the catch in the vicinity of electrodes 111g and 111h. The voltage pulse 409 of sufficient amplitude destroys the pathogen.

In one embodiment, Block 209 of the described procedure is flushing the CIS reservoir 105 so that the unbound catch 123 and any other molecular species 125 are removed. In another embodiment, this guarantees that when the controller 113 releases the fishing strings 115, only the catch 123 is present downstream for subsequent processing. The above process at Blocks 201, 203, 205, 207, and 209 can be repeated at Block 211.

Figure 5:
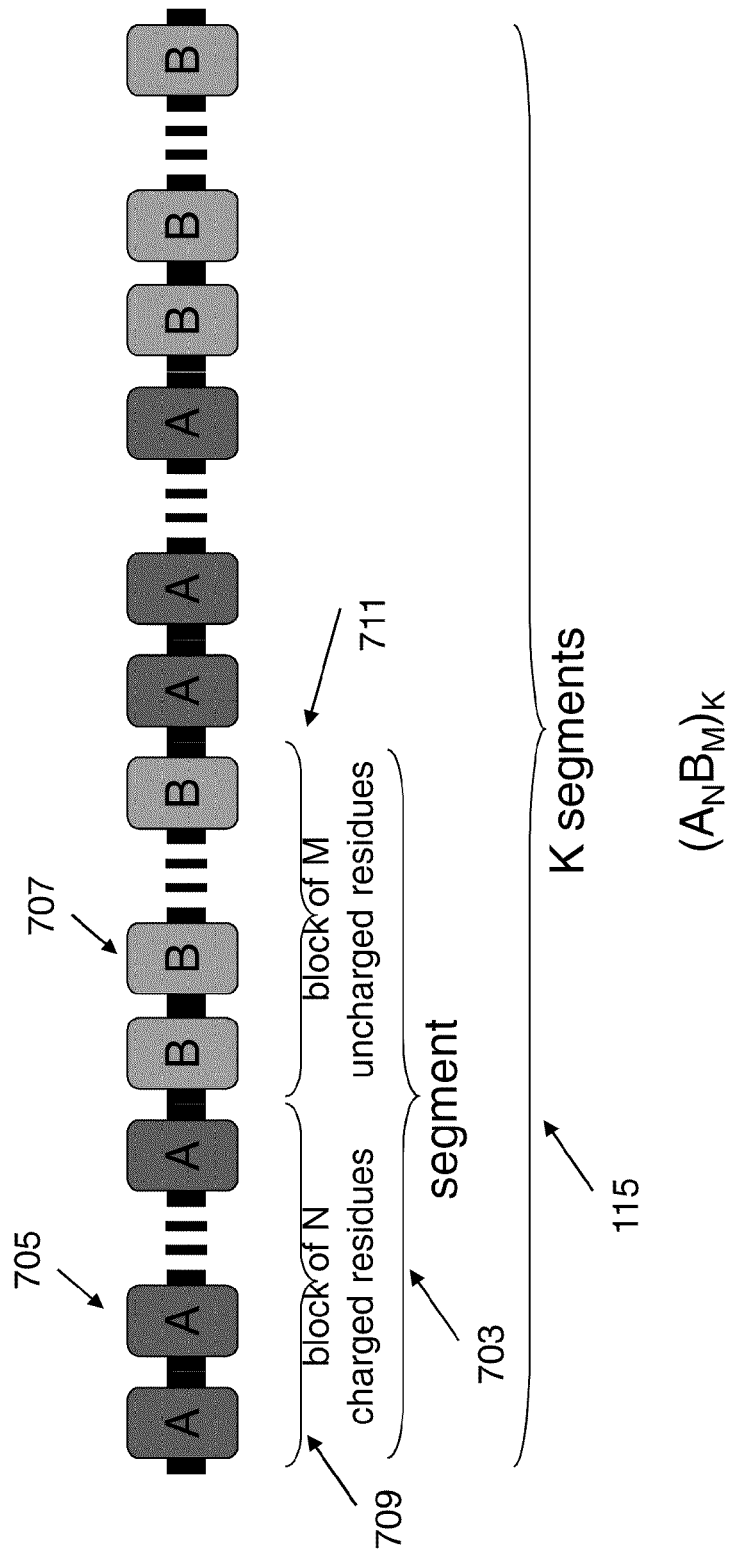
FIG. 5 is an exemplary embodiment of an engineered polypeptide for a material to be used as a "fishing string" for the nanopore capture system of FIG. 1.

In one embodiment, a variety of charged polymer molecules can be used as fishing strings 115. For example, one possible embodiment uses engineered polypeptides. FIG. 5 shows a polypeptide fishing string 115 consisting of K segments.

In one embodiment, each segment 703 consists of a block 709 of N charged amino acid residues A 705 and a block 711 of M uncharged amino acid residues B 707. In another embodiment, charged residues can be lysine, arginine, histidine, and/or the like that are positively charged, or aspartate, glutamate, and/or the like that are negatively charged. In another embodiment, uncharged residues can be polar serine, threonine, cysteine, asparagine, glutamine, and/or the like.

In one embodiment, the choice is determined by their hydrophilicity which would prevent the polypeptide from forming a tertiary structure, an undesirable feature for a fishing string 115. In another embodiment, the residues in each block do not need to be of same type. In another embodiment, the system 100 emphasizes the importance of large block sizes N and M for practical applications because larger distance between charges relaxes requirements on the separation between control electrodes of the stator and their thickness, making the linear motor easier to manufacture.

Figure 6:
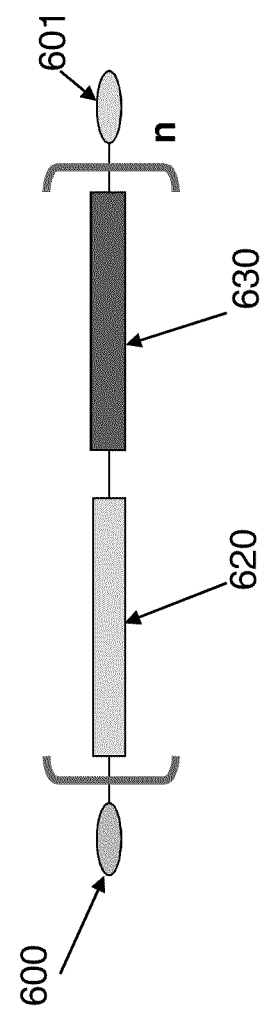
FIG. 6 is exemplary embodiments of non-biological molecules as materials or "fishing strings" for the nanopore capture system of FIG. 1.

Another fishing string embodiment is a synthetic polymer consisting of repeating units of charged and uncharged moieties. FIG. 6 illustrates the general structures of this synthetic polymer in which segment 600 and 601 are the end groups of the polymer which can be attached to the bait species. The end group 600 and 601 could be the same or different. Segment 620 is the uncharged moiety and segment 630 is the charged. As examples of each segment, the end groups 600 and 601 can be chosen from functionalities like hydroxyl (OH), carboxylic (—CO2H), or amine (—NH2), and/or the like functionality. The uncharged segment 620 can be long chain alkyl, alkoxy like polyethyleneoxide, and/or the like, and the charged segment is represented by conjugated aromatic chains like oligothiophenes, oligopyrrole, oligoaniline, and/or the like, all of which can be doped with a variety of reagents and acquire electrical charges.

In one embodiment, the fishing string 115 presents a variety of bait species. FIG. 7 outlines some bait species 901 capable of molecular recognition. Antibody-based bait 903 can identify and bind to antigens—viruses and bacteria. Nucleic acid binding protein baits 905 can, possibly specifically, attach to single or double stranded DNA molecules, RNA molecules, and/or the like.

In one embodiment, for a polypeptide-based fishing string 115, different domains of a single protein can serve as a fishing string and bait 121 simultaneously, simplifying the manufacturing. In another embodiment, single strands of nucleic acids can be used as bait 907 to catch complementary strands by sequence specific hybridization.

Figure 8A:
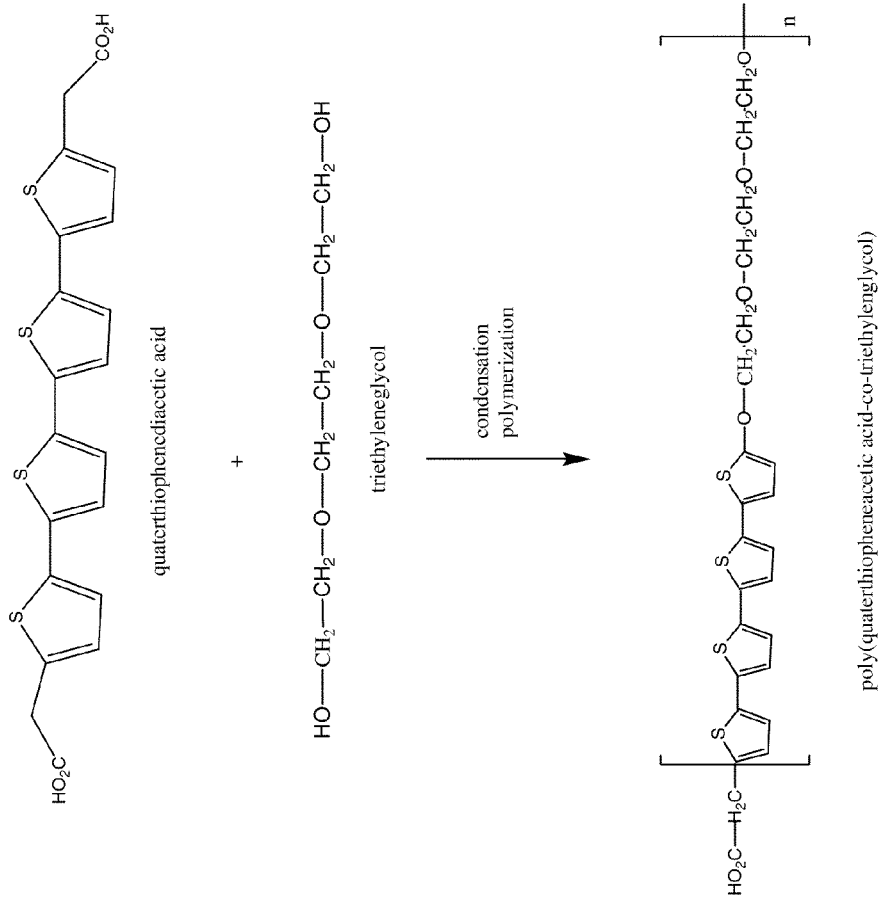
FIGS. 8a and 8b is a copolymer having charged moiety for the material to be used as fishing strings in the nanopore capture system of FIG. 1.
Figure 8B:
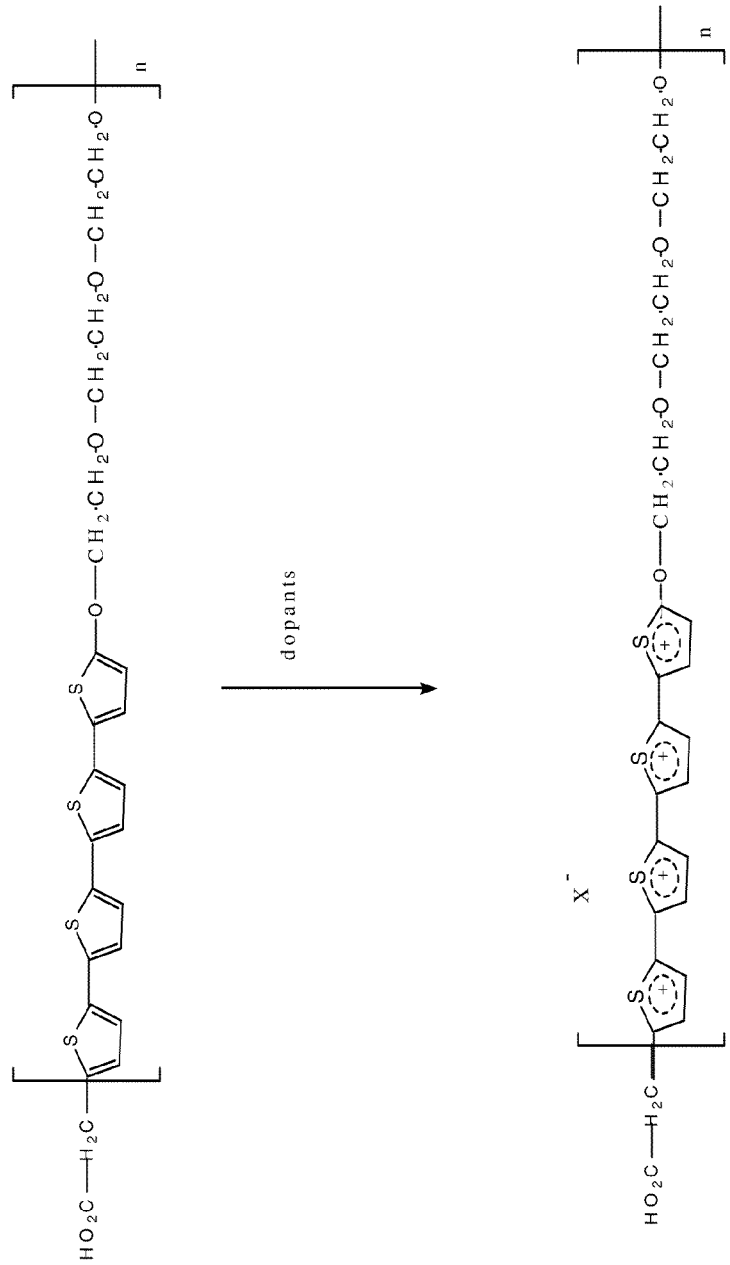

In one embodiment, covalent bonds between DNA and protein can be formed enabling robust connection between the fishing string 115 and the bait 123. In another embodiment illustrated in FIGS. 8a and 8b, a copolymer having charged moiety is shown.

Figure 9:
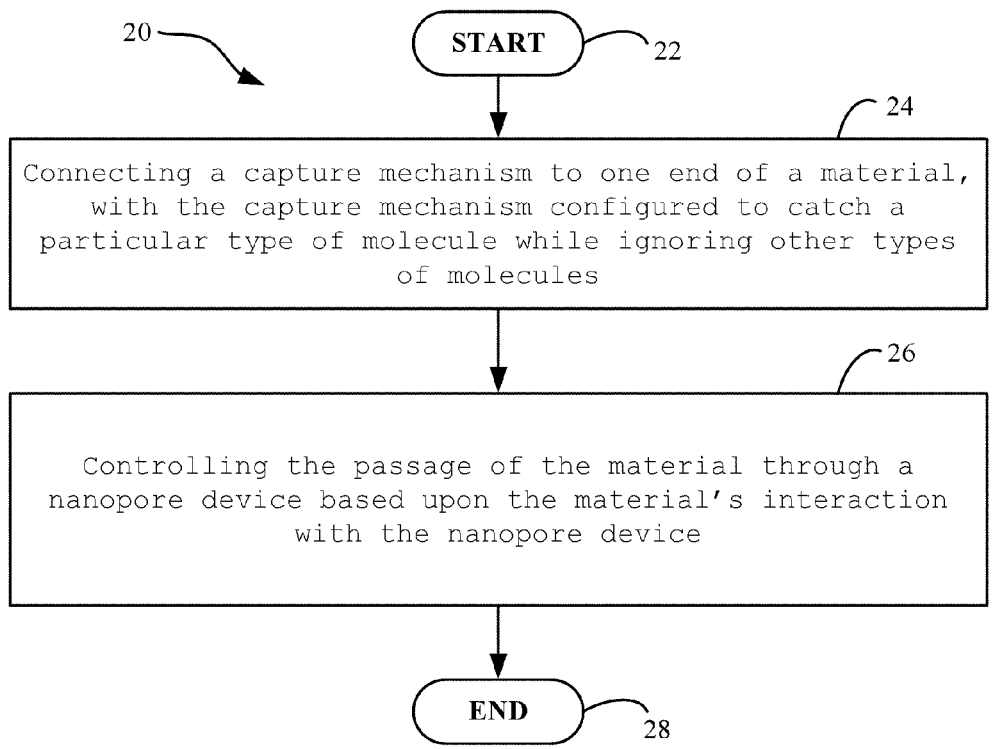
FIG. 9 is a flowchart illustrating another method aspect in accordance with the invention.

Another aspect of the invention is a nanopore capture system method, which is now described with reference to flowchart 20 of FIG. 9. The method begins at Block 22 and may include connecting a capture mechanism to one end of a material, with the capture mechanism configured to catch a particular type of molecule while ignoring other types of molecules at Block 24. The method may also include controlling the passage of the material through a nanopore device based upon the material's interaction with the nanopore device at Block 26. The method ends at Block 28.

Figure 10:
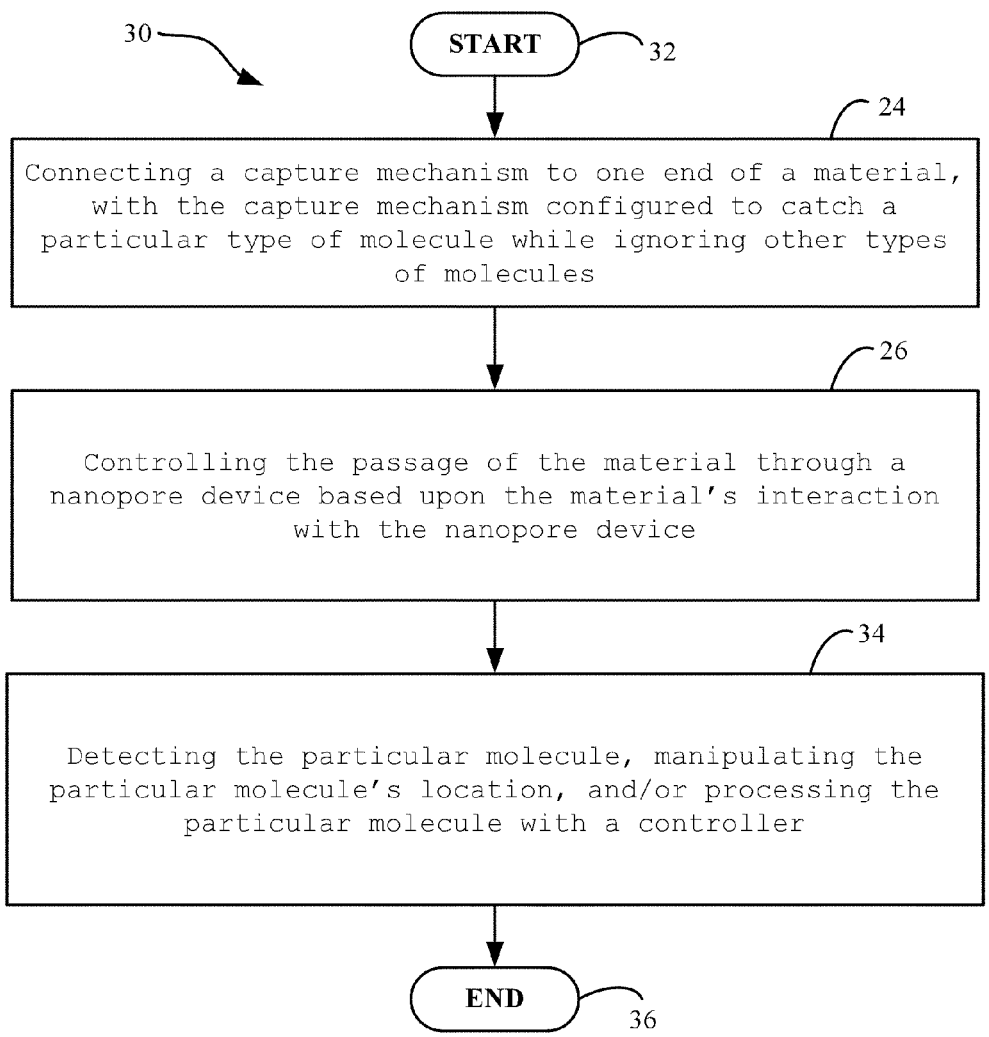
FIG. 10 is a flowchart illustrating method aspects according to the method of FIG. 9.

In another method embodiment, which is now described with reference to flowchart 30 of FIG. 10, the method begins at Block 32. The method may include the steps of FIG. 9 at Blocks 24 and 26. The method may additionally include detecting the particular molecule, manipulating the particular molecule's location, and/or processing the particular molecule with a controller at Block 34. The method ends at Block 36.

Figure 11:
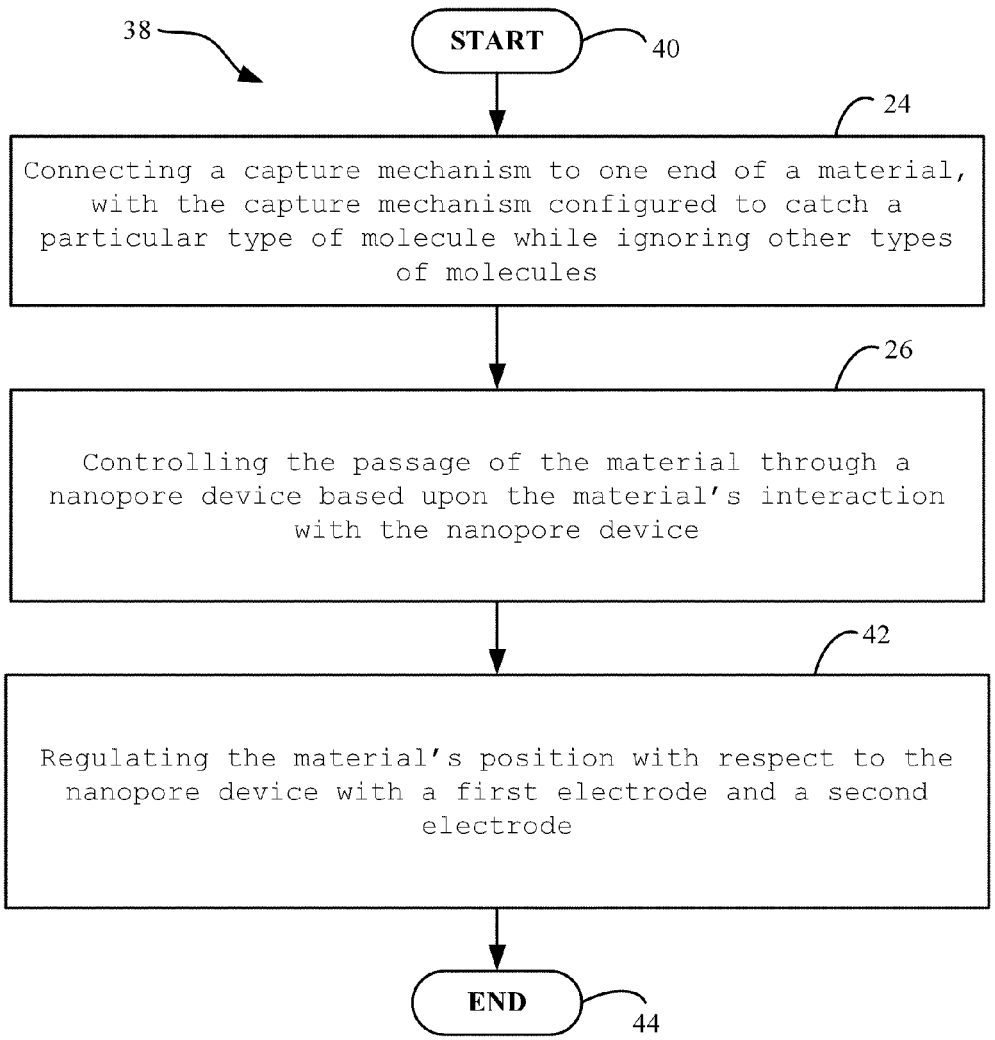
FIG. 11 is a flowchart illustrating method aspects according to the method of FIG. 9.

In another method embodiment, which is now described with reference to flowchart 38 of FIG. 11, the method begins at Block 40. The method may include the steps of FIG. 9 at Blocks 24 and 26. The method may additionally include regulating the material's position with respect to the nanopore device with a first electrode and a second electrode at Block 42. The method ends at Block 44.

Figure 12:
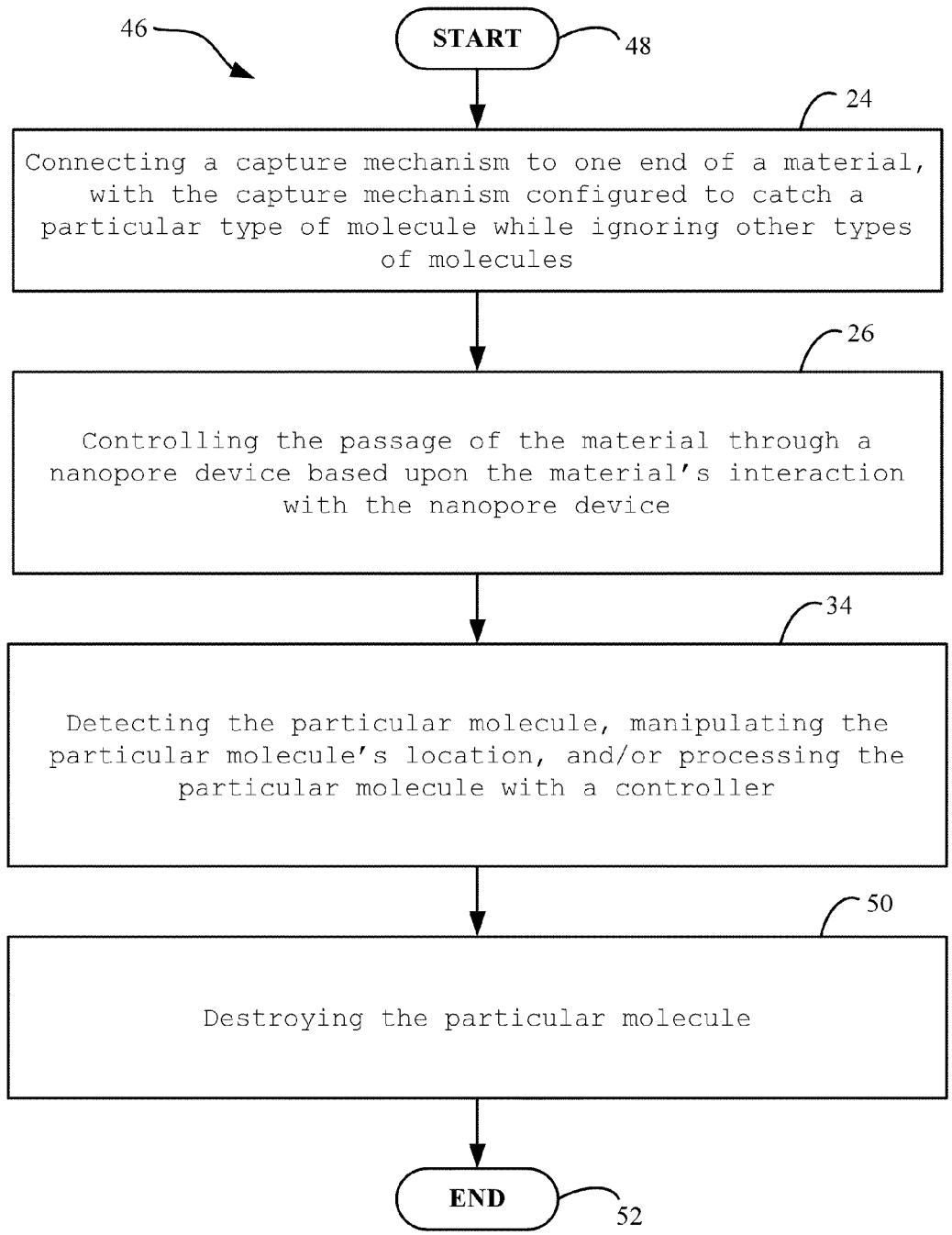
FIG. 12 is a flowchart illustrating method aspects according to the method of FIG. 10.

In another method embodiment, which is now described with reference to flowchart 46 of FIG. 12, the method begins at Block 48. The method may include the steps of FIG. 10 at Blocks 24, 26, and 34. The method may additionally include destroying the particular molecule at Block 50. The method ends at Block 52.

Figure 13:
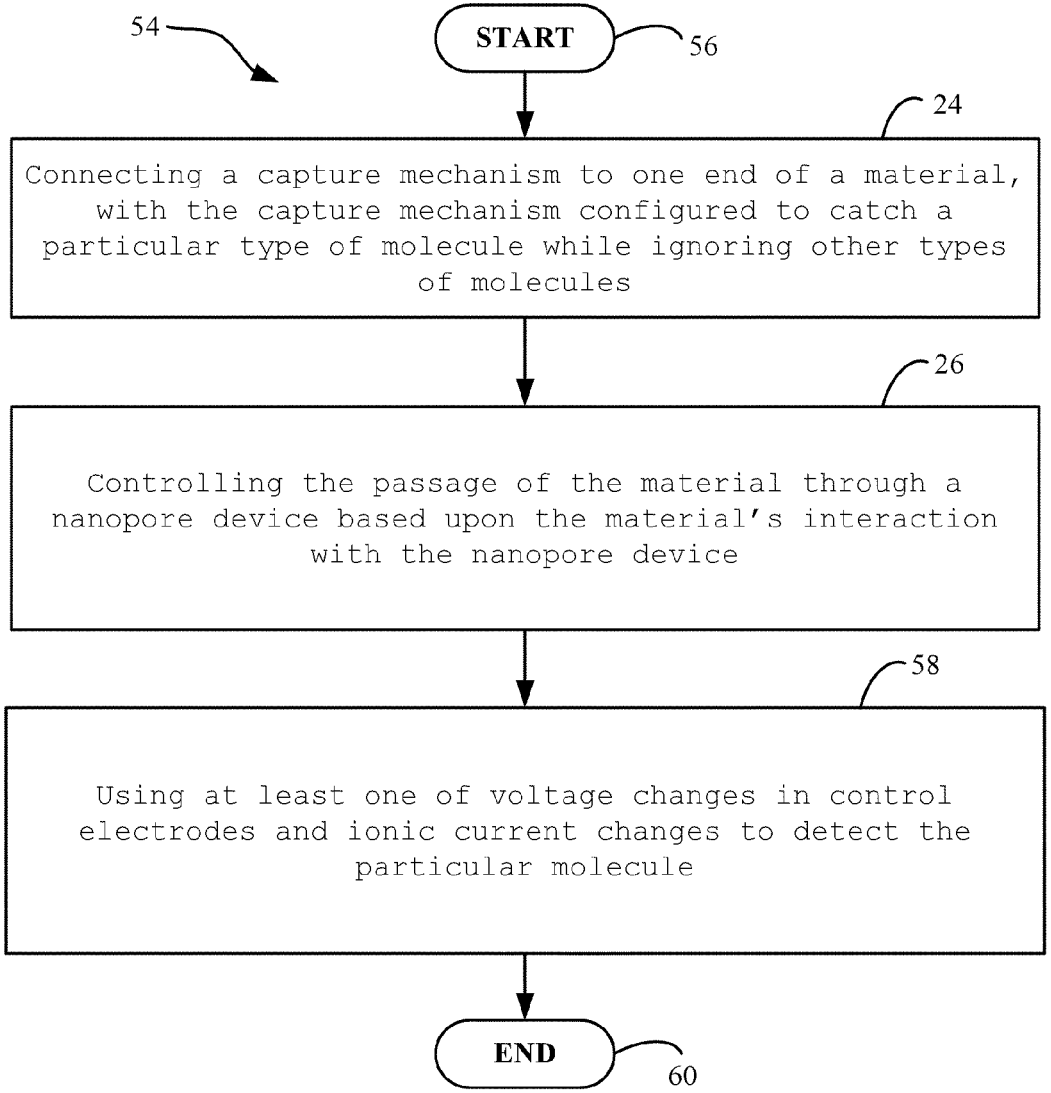
FIG. 13 is a flowchart illustrating method aspects according to the method of FIG. 9.

In another method embodiment, which is now described with reference to flowchart 54 of FIG. 13, the method begins at Block 56. The method may include the steps of FIG. 9 at Blocks 24 and 26. The method may additionally include using at least one of voltage changes in control electrodes and ionic current changes to detect the particular molecule at Block 58. The method ends at Block 60.

Another aspect of the invention is an embodiment in which a polymer material 115 is configured to pass through a nanopore device 101 in a controlled manner based upon its interaction with the nanopore device. The embodiment includes a capture mechanism 121 connected to one end of the polymer material 115, with the capture mechanism configured to catch a particular type of molecule 123, while ignoring other types of molecules 125. The embodiment also includes a controller 113 to detect the particular molecule 123 and/or manipulate the particular molecule's location.

Another aspect of the invention is an embodiment in which a material 115 is configured to pass through a nanopore device 101 in a controlled manner based upon its interaction with the nanopore device. The embodiment includes a capture mechanism 121 connected to one end of the material 115, with the capture mechanism configured to catch a particular type of molecule 123 while ignoring other types of molecules 125. The embodiment also includes a controller 113 to detect the particular molecule 123 and/or manipulate the particular molecule's location based upon voltage changes in control electrodes 111a-111n and/or ionic current changes.

In view of the foregoing, the system 100 provides a nanopore capture system where the fishing line polymer 115 is functionalized with a "bait" 121 that is capable of molecular recognition of other molecular species 123 ("catch"). As a result, molecules 123 that do not have localized charges periodically located along its chain can be manipulated using the nanopore capture system 100.

It should be noted that in some alternative implementations, the functions noted in a flowchart block may occur out of the order noted in the figures. For instance, two blocks shown in succession may, in fact, be executed substantially concurrently, or the blocks may sometimes be executed in the reverse order, depending upon the functionality involved because the flow diagrams depicted herein are just examples. There may be many variations to these diagrams or the steps (or operations) described therein without departing from the spirit of the invention. For example, the steps may be performed concurrently and/or in a different order, or steps may be added, deleted, and/or modified. All of these variations are considered a part of the claimed invention.

Furthermore, the use of the terms a, an, etc. do not denote a limitation of quantity, but rather denote the presence of at least one of the referenced item. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A system comprising:
a polymer material configured to pass through a nanopore device in a controlled manner based upon its interaction with the nanopore device;
a capture mechanism connected to one end of the polymer material, the capture mechanism configured to catch a particular type of molecule while ignoring other types of molecules; and
a controller to at least one of detect the particular molecule and manipulate the particular molecule's location.

2. The system of claim 1 wherein the polymer material comprises one of a polypeptide and a polynucleotide.

3. The system of claim 1 wherein the capture mechanism comprises at least one of an antibody, a deoxyribonucleic acid binding protein, an oligonucleotide, an aptamer and nucleic acid fragments for complementary strand hybridization.

4. The system of claim 1 wherein the controller processes the particular molecule.

5. The system of claim 1 further comprising:
a first electrode adjacent one side of the nanopore device;
a second electrode adjacent the other side of the nanopore device, and the first electrode and the second electrode are configured to regulate the polymer material's position with respect to the nanopore device.

6. The system of claim 1 wherein the controller applies a voltage pulse to the particular molecule.

7. The system of claim 6 further comprising a CIS reservoir adjacent one side of the nanopore device that is flushed after the voltage pulse is applied to the particular molecule.

8. The system of claim 1 wherein the controller detects the particular molecule based upon at least one of voltage changes in control electrodes and ionic current changes.

9. A system comprising:
a material configured to pass through a nanopore device in a controlled manner based upon its interaction with the nanopore device;
a capture mechanism connected to one end of the material, the capture mechanism configured to catch a particular type of molecule while ignoring other types of molecules; and
a controller to at least one of detect the particular molecule and manipulate the particular molecule's location based upon at least one of voltage changes in control electrodes and ionic current changes.

10. The system of claim 9 further comprising:
a first electrode adjacent one side of the nanopore device;
a second electrode adjacent the other side of the nanopore device, and the first electrode and the second electrode are configured to regulate the material's position with respect to the nanopore device.

* * * * *